United States Patent [19]

Mekalanos

[11] Patent Number: 5,631,010
[45] Date of Patent: May 20, 1997

[54] GENETICALLY STABLE CHOLERA VACCINES WITH DELETIONS OF CTXA, RECA AND ATTRS1

FIG. 3C  Type 2 Deletion

FIG. 3D

Peru-2
Bang-2
Bah-2

GENETICALLY STABLE CHOLERA VACCINES WITH DELETIONS OF CTXA, RECA AND ATTRS1

This invention was made with the support of the U.S. government and the government therefore has certain rights in the invention.

This is a continuation of application Ser. No. 08/083,388, filed Jun. 28, 1993, which is a continuation of application Ser. No. 07/909,382, filed Jul. 6, 1992; both of which are abandoned.

BACKGROUND OF THE INVENTION

The field of invention is *Vibrio cholerae* vaccines.

After more than 100 years of research on cholera, there remains a need for an effective cholera vaccine. There have been six pandemics of this disease caused by strains of *V. cholera* belonging to the "Classical" biotype. The etiological agents of the current (seventh) pandemic belong to the "El Tor" biotype (Finkelstein, Crit. Rev. Microbiol 2:553–623, 1973, Wachsmuth et al., The Lancet 337:1097–1098, 1991). Recently the seventh pandemic has extended to a new locale, that of South America. Beginning in January of 1991, an epidemic of cholera resulted in greater than 250,000 cases and over 2,000 deaths in Peru, Ecuador, Columbia, and Chile. Before this epidemic it was estimated that over 200,000 cases of cholera occurred per year mainly in India, Bangladesh, Africa and Western Asia (Tacket et al., Cholera Vaccines. In *Vaccines: New Approaches to Immunological Problems*, Ellis, R. W., editor, Butterworth-Heinemann, Boston, 1992).

Because natural infection by and recovery from cholera induces immunity lasting at least 3 years (Tacket et al., Supra; Levine et al., J. Infect. Dis. 143:818–820, 1981; Cash et al., J. Infect. Dis. 130:325–333, 1974), much effort has been made to produce live, attenuated cholera vaccines that when administered orally would mimic the disease in its immunization properties but would not cause adverse symptoms or reactions in the immunized individual (i.e., display low reactogenicity). Vaccines of this type involve deletion mutations that inactivate the gene encoding the A subunit of cholera toxin, a protein which is responsible for most of the diarrhea seen in this disease (Mekalanos et al., Proc. Natl. Acad. Sci. USA 79:151–155, 1982; Mekalanos et al., Nature 306:551–557, 1983; Kaper et al., Nature 308:655–658, 1984; Kaper et al., Biotechnology 2:345, 1984; Pierce et al., Infect. Immun. 55:477–481, 1987; Taylor et al., Vaccine 6:151–154, 1988; Levine et al., Infn. Immun. 56: 161–167, 1988; Herrington et al. J. Exper. Med. 168:1487–1492, 1988; Levine et al., Lancet ii:467–470, 1988; Kaper et al., Res. Microbiol. 141:901–906, 1990; Pearson et al., Res. Microbiol. 141:893–899, 1990). See also Mekalanos, U.S. Pat. Nos. 5,098,998 and 4,882,278, and Kaper et al., U.S. Pat. No. 4,935,364, hereby incorporated by reference. The major issues associated with cholera vaccines are safety, stability and their degree of antigenicity.

With regard to the toxin genes of *V. cholerae*, the genetic diversity among toxigenic and non-toxigenic strains has been examined by Chen et al. (1991, Epidemiol. Infect. 107:225). Mekalanos (1983, Cell 35:253) reports on the duplication and amplification of *V. cholerae* toxin genes, and Miller et al. (1984, Proc. Natl. Acad. Sci. USA 81:3471) discusses transcriptional regulation of the toxin genes. Other *V. cholerae* genes whose products may play a role in the pathogenicity of this organism include the toxin-coregulated pilus genes (Shaw et al., 1990, Infect. Immun. 8:3042; Sharma et al., 1989, Vaccine, 7:451;Sun et al., 1990, J. Infect. Dis. 161:1231; Hall et al., 1991, Infect. Immun. 59:2508; Taylor et al., 1987, Proc. Natl. Acad. Sci. USA 84:2833), and the gene encoding the intestinal colonalization factor (Taylor et al., 1988, Vaccine 6:151).

SUMMARY OF THE INVENTION

The invention features a nontoxigenic genetically stable mutant strain of *V. cholerae* which is useful as a live, oral vaccine for inducing immunological protection against cholera. The mutant strain is a genetically engineered mutant which lacks DNA encoding a functional ctxA subunit and also lacks any functional attRS1 sequences. By attRS1 sequences is meant a 17 base pair sequence contained within the CTX genetic element that is required for recombination and amplification of the CTX genetic element, or enough of that sequence to enable such recombination and amplification. Mutants which "lack any functional attRS1 sequences" are those which substantially cannot undergo effective site-specific recombination with attRS1-containing vehicles, because the wild type attRS1 sequences are wholly deleted or are sufficiently deleted or mutated to prevent such recombination. As a result, *V. cholerae* strains according to the invention are safer because they cannot recombine with wild type attRS1-containing vehicles which include the ctxA-encoding DNA.

The invention also features a method of making the above described *V. cholerae* strain. The method involves introducing a plasmid into a wild type *V. cholerae* which contains a fragment of *V. cholerae* DNA containing a mutation in the ctxA and attRS1 sequences. The *V. cholerae* DNA fragment is capable of recombining with wild type *V. cholerae* DNA inside the organism to generate the mutant strain.

In preferred embodiments, the mutant strain of *V. cholerae* belongs to the El Tor biotype, and more preferably, the Inaba or Ogawa serotype. Preferably, the mutant lacks all of the CTX core and attRS1 sequences and more preferably the mutant strain is Peru-2, Bang-2 or Bah-2 as described below.

Mutant strains according to the invention optionally include additional mutations introduced to improve the safety and/or the immunogenicity of the vaccine. Such additional mutations include, but are not limited to, inactivation of the recA gene encoded by the strain, and the introduction of additional genes into the *V. cholerae* chromosome, preferably into the *V. cholerae* lacZ gene. Such additional genes include a gene encoding the B subunit of *V. cholerae* or any heterologous antigen such as the B subunit of Shiga-like toxin, or a gene encoding an *E. coli* CFA antigen. By heterologous antigen is meant any antigen that is not normally expressed by *V. cholerae*. Preferably, the mutant strain having additional mutations is Peru-3, Peru-4, Peru-5, Bang-3, Bang-5, Bah-3, Bah-4 and Bah-5.

By a ctxA subunit is meant the A subunit of the cholera toxin which is responsible, when functional, for many of the symptoms of cholera (e.g., nausea, diarrhea etc.). Most preferably, the strains include deletion of the entire so-called "core genetic element", includes not only the ctxA/B, but also a region known as ICF and ZOT, described in greater detail below.

The invention also features a killed, oral cholera vaccine comprising at least a first and a second *V. cholerae* strain, wherein at least two of the strains are different serotypes and all strains in the mixture lack DNA encoding a functional ctxA subunit. The vaccine also contains cholera toxin B subunit produced by at least one of the serotypes. Preferably, one of the serotypes in the vaccine is an Ogawa serotype and another of the serotypes is an Inaba serotype. Most preferably, the killed oral vaccine comprises Bah-3 and either Peru-3 or Bang-3, or both Peru-3 and Bang-3, defined below.

The invention also features a method of making a killed *V. cholerae* vaccine. The method involves growing at least a first and a second *V. cholerae* strain, wherein each strain in the mixture lacks DNA encoding a functional ctxA subunit. The strains are then collected from the growth medium and the cells are killed. Cholera toxin B subunit, produced by at least one of the strains is obtained from the medium in which the strain was propagated and is added to the killed cells. The mixture of killed bacteria and cholera toxin B subunit is then suspended in a physiologically acceptable carrier.

Mutants such as those described above are useful as cholera vaccines and are improved in their genetic properties compared with previous vaccines.

Other features and advantages of the inventions will be apparent from the following description of preferred embodiments thereof, and from the claims.

DETAILED DESCRIPTION

The drawings will first be briefly described.

The Drawings FIG. 1 is a schematic diagram of the CTX genetic elements of toxigenic *V. cholerae* strains P27459-Sm, C6709-Sm and E7946-Sm. The filled in boxes represent RS1 sequences. Between the RS1 sequences is a region shown as an open box (called the core region) which contains the ctxAB genes and genes encoding zot, the intestinal colonization factor (ICF). At the ends of the RS1 sequences are filled in circles that represent copies of sequences that match 16 out of 17 bases with the 17 base pair sequence attRS1 (CCTAGTGCGCATTATGT) [SEQ.ID.NO:1]. Although the CTX elements of the three strains vary in their structure based on the number of copies of the RS1 and core regions, it should be noted that these elements are inserted into the same chromosomal site in all El Tor strains of *V. cholerae*.

FIG. 2(A) and B.

FIG. 3A–D.

FIG. 5 is a diagrammatical representation of the generation of pJM84.1 and pJM84.2. A 0.6 kb fragment encoding a promoterless B-subunit was generated by PCR. This DNA was ligated into pCR100 and digested with SpeI/EcoRI. The resulting 0.6 kb restriction fragment was ligated into EcoRI/XbaI digested pVC100 and pRT41 vectors, yielding pJM1001 and pJM411, respectively. Each plasmid was digested with BamHI/EcoRI, treated with Klenow, flanked with XbaI linkers, and digested with XbaI. Purified fragments were ligated to XbaI digested pGP84, yielding pJM84.1 and pJM84.2.

FIG. 6 is a diagrammatical representation of the insertion of the ctxB into the chromosome. Non-replicative pJM84.1 was integrated into Peru-2, Bang-2 or Bah-2 by homologous recombination. Ampicillin resistant recombinant colonies were subsequently plated on medium which contained streptomycin without ampicillin, thus reducing the selective pressure for ampicillin resistance. The resulting ampicillin sensitive colonies were isolated and had selected for excision of DNA flanked by homologous recA DNA sequences.

The invention features attenuated strains of *V. cholerae* that can be used either as live or killed oral vaccines to protect individuals against cholera and potentially other diseases.

Attenuated derivatives of a *V. cholerae* strain C6709-Sm isolated from a cholera patient in Peru in 1991 have been constructed that can be used as live, oral cholera vaccines. The derivatives Peru-1 and Peru-2, carry small Type-1 (core) and large Type-2 deletions, respectively, which remove the DNA encoding the cholera toxin in addition to DNA encoding zot, an intestinal colonization factor (ICF) that is unrelated to cholera toxin. Because excessive intestinal colonization may be responsible for adverse side effects seen in humans administered earlier prototype live cholera vaccines, the deletion of genes encoding both cholera toxin and ICF in Peru-1 and Peru-2 will render these strains less reactogenic in vaccinees while they retain their immunogenic and therefore protective properties.

The larger Type-2 deletion present in Peru-2 also removes an insertion-like sequence called RS1 which is present in two or more copies as part of a larger DNA segment called the CTX genetic element. The RS1 sequence encodes a site-specific recombination system that can duplicate at a high frequency and cause insertion of the CTX element into the *V. cholerae* chromosome at a 17 base pair target site called attRS1. Sequences nearly identical to attRS1 (and apparently just as recombinationally active) exist at the ends of the RS1 sequences. These sequences are as follows:
attRS1 and flanking chromosomal sequences:
 5'-TAAACCTAGAGACAAAATGTTCCTAGTGCGCA-TTATGTATGTTATGTTAAAT-3' [SEQ.ID.NO:2]
Left side of RS1 and chromosomal junction:
 5'-TAAACCTAGAGACAAAATGTTCCTAGTGCGCA-TTATGTGGCGCGGCAT . . . RS1 . . . -3' [SEQ.ID.NO:3]
Right side of RS1 and chromosomal junction:
 5'-AAACCCTAGATTCCGCCGCCTTAGTGCGCATT-ATGTATGTTATGTTAAAT-3' [SEQ.ID.NO:4]
The attRS1 and a similar sequence present at the ends of RS1 are underlined. Note that the chromosomal sequence that flanks attRS1 is present on the left and the right side of RS1 with the only overlap being a 17 base pair sequence that is identical to attRS1 on the left end of RS1 and an 18 base pair sequence that matches 17/18 base pairs with attRS1.

Genetically engineered live attenuated cholera vaccines are theoretically safe only if they cannot revert or otherwise regain the capacity to produce cholera toxin. Strains which carry a single copy of the attRS1 sequence can efficiently acquire a new copy of the CTX element through DNA transfer by either P factor conjugation or bacteriophage transduction. Thus, deletions which render *V. cholerae* devoid of RS1 and attRS1 sequences can prevent a vaccine strain from reacquiring the CTX genetic element in nature through its own site specific recombination system. Such a deletion is present in strain Peru-2 and its derivatives.

Six mutant strains of *V. cholerae* with similar but not identical properties have been constructed. Four strains that carry the same two types of deletions (Type-1 and Type-2) as strains Peru-1 and Peru-2 were constructed in *V. cholerae* strains isolated from patients in Bangladesh (P27459-Sm) and Bahrain (E7946-Sm). These four derivatives, Bang-1, Bang-2, Bah-1 and Bah-2 are also the subject of the invention because they vary in colonization and/or other properties (e.g., serotype) and they are therefore potentially more suitable than the corresponding Peru strains for use as vaccines in other areas of the world.

Although the smaller Type-1 deletion present in the three strains Peru-1, Bang-1 and Bah-1 does not remove all copies of RS1, this particular deletion affects the intestinal colonization properties of some of these strains more severely than the larger deletion present in Peru-2, Bang-2 and Bah-2.

Construction of Type-2 Deletion Mutations

A Type-2 deletion removes all sequences corresponding to the CTX genetic element including RS1 sequences and all copies of the attRS1 sequence (FIG. 1). The Type-2 deletion was constructed by recombination between the chromosome of *V. cholerae* and the plasmid sequences cloned on plasmid pAR62 as shown in FIG. 2. Plasmid pAR62 is a derivative of plasmid pGP60 and carries a Type-2 deletion wherein the HindIII fragment shown in FIG. 2 was deleted. Plasmid pGP60 was constructed by first generating a genomic library of strain p27459 by inserting 20–30 kb Sau3A partially digested fragments into the BamHI site of plasmid pLAFR2 (Friedman et al., 1982, Gene 18:289). Colonies were screened by hybridization using probes derived from the ctx region (Mekalanos, 1983, Cell 35:253). A positive colony was picked and the plasmid which was isolated therefrom was named pGP60. Restriction enzyme analysis of this plasmid confirmed that it contained all of the CTX element sequences and additional flanking DNA. Plasmid pAR62 encodes resistance to tetracycline. This plasmid was introduced into a strain of *V. cholerae* by conjugation or electroporation followed by selection on media containing 3 μg/ml of tetracycline. Such a plasmid carrying strain was then screened by colony hybridization with radioactive L-3 probe prepared as described in Goldberg and Mekalanos (J. Bacteriol. 165:723–731, 1986). Colonies carrying the Type-2 deletion inserted into the chromosome did not hybridize to the L-3 probe and surprisingly, occurred at a high frequency (i.e., about 1% of the colonies screened). Southern blot analysis was used to confirm the presence of the expected deletions in these strains.

Construction of Core (Type-1) Deletions

A "core deletion" removes only sequences corresponding to the core of the CTX element but leaves behind a copy of the RS1 element on the chromosome (Goldberg et al., J. Bacteriol. 165:723–731, 1986) (FIG. 3.). These deletions occur spontaneously through homologous recombination between RS1 sequences located on the right side and left side of the core region as shown in FIG. 3. Colonies of *V. Cholerae* that contain core deletions can be identified in two ways. First, if the strain carries a selectable marker such as a gene encoding kanamycin resistance inserted in the core region, then the core deletion renders such a strain sensitive to kanamycin (Goldberg et al., J. Bacteriol. 165:723–731, 1986). Second, colonies that contain the core deletion can also be identified by colony hybridization using radioactive CT-1 probe which does not hybridize to strains carrying this deletion (Goldberg et al., J. Bacteriol. 165:723–731, 1986). By either method, colonies that carry these deletions occurred at a frequency of about 1 per 1000 colonies screened. Analysis by Southern blot hybridization was then used to confirm the expected deletions in these strains.

An Assay for Functional attRS1 Sequences Based Upon Integration of plasmid pGP52

The plasmid pGP52 is a suicide plasmid which is only capable of replicating in strains of *E. coli* such as SM10λpir (Pearson et al., 1990, Res. Microbiol. 141:893). Plasmid pGP52 was constructed by first digesting the plasmid pGP7 (Mekalanos, 1983, Cell 35:253) with ClaI and SphI. This plasmid contains two RS1 sequences (termed RS1 and RS2) derived from the *V. cholerae* strain E7946-Sm. A fragment of DNA which contained the RS1 sequences was cloned into pBR322 and the resulting plasmid was named pGP20. This plasmid was then digested with EcoRV (which cuts within the RS1 sequences). When this plasmid was religated a new plasmid termed pGP20R was generated containing a hybrid version of RS2 called RS2*, wherein the hybrid RS2 sequences were flanked by core sequences. An SspI-SphI fragment of RS2 was then subcloned into the suicide plasmid pJM703.1 which had been digested with NruI and SphI. The plasmid pJM703.1 is described in Miller et al. (Proc. Natl. Acad. Sci. USA 81:3471). The resulting plasmid was called pGP52. A diagram depicting the construction of pGP52 is shown in FIG. 4.

When pGP52 is transferred by conjugation into *V. cholerae* strains which contain attRS1 sequences, it integrates into the *V. cholerae* chromosome by means of a site-specific recombination event between the attRS1 sequence on the chromosome and the attRS1 sequence present on the plasmid. Integration events such as these can be quantitated by determiquantitated by determining the number of colonies that stably maintain (i.e., are non-selected) ampicillin resistance because resistance to ampicillin is encoded by pGP52. Confirmation of integration can be obtained in Southern blot hybridization experiments. If the *V. cholerae* strain to be tested has functional attRS1 sequences then integration will be observed in the test. If the strain does not contain functional attRS1 sequences, integration will not occur.

In order to assess the ability of the various vaccine candidates to serve as recipients for pGP52, the following experiments were performed. Donor *E. coli* strain SM10λpir pGP52 was mixed with the recipient *V. cholerae* test vaccine strain in 5 ml of Luria broth at concentration of $10^7$ cells from each strain per culture. The mixture was incubated at 37° C. for 5 hours at which time it was diluted 1:100 into fresh Luria broth containing 100 μg/ml of streptomycin. The purpose of the streptomycin is to select against the *E. coli* donor strain by killing it. Thus, only the streptomycin resistant *V. cholerae* recipient strains are capable of growth. This culture was incubated until the growth rate of the cells reached saturation. The cultures were diluted again and further incubated until each cell had replicated a total of 20 times in the absence of any positive selection for pGP52. This culture was then diluted and plated on two separate media compositions in order to quantitate the number of viable colonies. One of these media is Luria broth which does not contain any antibiotics. The number of colonies appearing on these plates represents the total number of cells in the culture. The other medium is Luria broth which contains ampicillin. The number of colonies appearing on these plates represents the number of integration events that occurred following conjugation. The results are expressed as a ratio of stable integration events/total number of viable cells and are presented in Table 1 below.

TABLE 1

Representative Integration Data on Peru Vaccine Strains

| Strain | Stable Integration events/total # viable cells |
| --- | --- |
| Peru-1 | $5.2 \times 10^{-5}$ |
| Peru-2 | Not detectable ($<5 \times 10^{-8}$) |
| Peru-3 | Not detectable ($<5 \times 10^{-8}$) |
| Peru-4 | Not detectable ($<5 \times 10^{-8}$) |
| Peru-5 | Not detectable ($<5 \times 10^{-8}$) |

Based on these data it is evident that strain Peru-1, which contains two copies of the attRS1 sequences is capable of integrating the plasmid pGP52 into its chromosome at a frequency that is at least 1000-fold higher than any of the other strains tested, all of which lack any attRS1 sequences.

Serological Characterization of Vaccine Strains

The vaccine strains Peru-2, Bang-2, and Bah-2 were characterized further in terms of their serological and colonization properties. The data presented in Table 2 demonstrate that each derivative retained its expected serotype (i.e., the serotype of each of the mutants respective parental strain) when freshly harvested bacterial cells were tested by slide agglutination using Difco V. cholerae 01 Inaba or Ogawa typing serum. This result indicates that these strains still express LPS antigens. Other tests demonstrate that these mutant strains are motile, prototrophic, and still express Tcp pili. Thus, the mutants express a number of properties that are important for their ability to be useful as live vaccine strains.

Colonization properties of the Vaccine Strains and Core Deletion Mutants

To test the colonization properties of these vaccine strains, a mouse intestinal competition assay was used as described in Taylor et al. (Proc. Natl. Acad. Sci. USA. 84:2833–2837, 1987) which has been shown to correlate accurately with the colonization properties of mutant strains when they are subsequently tested in human volunteers (Herrington et al., J. Exper. Med. 168:1487–1492, 1988). The assay measures differences in colonization of a mutant strain by comparing its ability to compete for growth and survival with another closely related or isogenic strain. In this assay, the mutant and competing strains were mixed in a ratio of approximately 1:1 and then approximately one million cells of this mixture were introduced to the stomach of 3–5 day old suckling CD-1 mice. After 24 hours, the mice were sacrificed, the intestine was dissected, homogenized, and plated on bacteriological media containing streptomycin which selects for both strains. Colonies that grew after overnight incubation are then tested for additional markers which differentiate the mutant strain from the competing strain (i.e., resistance to kanamycin or hybridization with appropriate radioactive DNA probes; see legend of Table 3).

As shown in Table 3, Bang-2, and Bah-2 both exhibited a mild intestinal colonization defect that resulted in approximately 4–13 fold greater recovery of the isogenic competing strains than the mutant strains after 24 hours of growth in the mouse intestine. Also shown in Table 3, are results from competition assays involving core deletion mutant strains Peru-1, Bang-1 and Bah-1. Like the Type-2 deletion strains Bang-2 and Bah-2, these core deletion mutants were defective in colonization relative to their isogenic competing strains. Because core deletions remove sequences corresponding to the core of the CTX element (FIG. 1 and 3), these data suggest that the core of CTX element encodes an "intestinal colonization factor, or ICF". Cholera toxin by itself is not an ICF. Strains SM44 and SM115 which are defective in cholera toxin production due to a deletion in the ctx genes and insertion of a gene encoding kanamycin resistance as described in Goldberg and Mekalanos (J. Bacteriol. 165:723–731, 1986) outcompete their respective mutant strains (Bang-1, Bang-2 and Bah-1, Bah-2) in the intestinal competition assay. Thus, it is apparent that SM44 and SM115 make ICF even though they do not produce cholera toxin, while the mutants do not. Furthermore, because the CTX core region was the only DNA that is deleted in both core as well as Type-2 deletions and mutants carrying both types of deletions were similarly defective in colonization, it can also be concluded that ICF is encoded by the core region of the CTX element as shown in FIG. 1.

Recently, a new toxin called ZOT has been found to be encoded by the core region (Baudry et al., 1992, Infect. Immun. 60:428–434). We have evidence that mutations in the ZOT gene do not produce the colonization defect observed in Type-1 or Type-2 deletion mutants. Accordingly, ICF is designated as a separate and distinct property from ZOT. The vaccine strains described herein carrying Type-1 or Type-2 deletions are defective in ICF.

In contrast, strain Peru-2 exhibited no significant defect in intestinal colonization relative to its competing strain C6709-Sm (Table 2). However, the total cell yield of either strain C6709-Sm or Peru-2 in the mice was typically 10–100 fold less than strains SM44 or SM115, suggesting that the Peru strain C6709-Sm and its derivative Peru-2 may already carry an undefined colonization defect. Since deletion of the core of all or part of the CTX element did not cause a further defect in the colonization of either strain Peru-1 or Peru-2, it can be concluded that strain C6709-Sm is partially defective in ICF already even though it carries DNA sequences that correspond to the CTX core region. Deletion of the entire CTX region as defined by the Type-2 mutations present in strains Peru-2, Bang-2 and Bah-2 assures that the genes for ICF cannot reactivate and become functional in the vaccine derivatives. The Type-2 deletion of ICF genes apparently causes a mild colonization defect. Such may be useful as an attenuating mutation in cholera vaccine development, because wild type ICF may be responsible for undesirable levels of toxicity.

TABLE 2

| Properties of Mutant Strains | | | |
|---|---|---|---|
| Mutant Strains | Parental Strain* | Serotype | Type of Deletion |
| Peru-2 | C6709-Sm | Inaba | Type-2 |
| Bang-2 | P27459-Sm | Ogawa | Type-2 |
| Bah-2 | E7946-Sm | Inaba | Type-2 |

*Note that the designation "Sm" behind the strain name refers to streptomycin resistance. This is a spontaneously selected strain which is resistant to 100 μ/ml of streptomycin and was the result of a spontaneous point mutation in the gene for a ribosomal protein. This resistance marker is not associated with a plasmid or transposon and is therefore not transmissible to enteric flora. Because all mutant strains are derived from the indicated parental strains, all mutant strains are also resistant to streptomycin.

TABLE 3

Infant Mouse Colonization Competition Assays[a]

| Mutant Strain | Competing Strain | Input Ratio Mutant/ Competing Strain | Output Ratio Mutant/ Competing Strain |
|---|---|---|---|
| Bang-2 | SM44[b] | 0.61 | 0.16 |
| Bah-2 | SM115[c] | 0.92 | 0.07 |
| Peru-2 | C6709-Sm[d] | 0.74 | 0.65 |
| Bang-1 | SM44[b] | 0.85 | 0.05 |
| Bah-1 | SM115[c] | 0.61 | 0.04 |
| Peru-1 | C6709-Sm[d] | 0.89 | 0.94 |

[a]Infant mouse colonization assays were performed according to the method described in Taylor et al. (Proc. Natl. Acad. Sci. USA. 84:2833–2837, 1987). The ratio of strains was determined by either differential sensitivity to antibiotics or by colony hybridization with appropriate probes as described in the additional footnotes below.
[b]Strain SM44 has been described in Goldberg and (J. Bacteriol. 165:723–731, 1986) and is a kanamycin resistant derivative of the parental strain P27459-Sm. The gene encoding kanamycin resistance in SM44 was inserted in the ctx locus. Because Bang-1 and Bang-2 were derivatives of P27459-Sm competition with SM44 measures colonization differences that can be attributed to the effect of the Type 2 rather loss of ctx. Strains Bang-1 and Bang-2 were sensitive to kanamycin and were differentiated from SM44 in these competitions assays by scoring colonies for resistance to 30 μg/ml kanamycin.
[c]Strain SM115 has been described in Goldberg and Mekalanos (J. Bacteriol. 165:723–731, 1986) and is the kanamycin resistant derivative of the parental strain E7946-Sm. The gene encoding kanamycin resistance in SM115 was inserted in the ctx locus. Because Bah-1 and Bah-2 are derivatives of P27459-Sm competition with SM115 measures colonization differences that can be attributed to the effect of the Type 2 deletion rather than loss of ctx. Strains Bah-1 and Bah-2 were sensitive to kanamycin and were differentiated from SM115 in these competitions assays by scoring colonies for resistance to 30 μg/ml kanamycin.
[d]Strain C6709-Sm is the parental strain of Peru-1 and Peru-2. Peru-2 carries a Type -2 deletion while Peru-1 carries a core deletion. Both these deletions remove the ctx genes and thus both Peru-1 and Peru-2 were negative in colony hybridization blots when probed with the CT-1 probe described in Goldberg and Mekalanos (J. Bacteriol 165:723–731, 1986) while strain C6709-Sm was positive using the same probe. Thus, both Peru-1 and Peru-2 were differentiated from C6709-Sm in these competitions assays by scoring colonies for hybridization with the CT-1 probe.

The mutant strains described can be further improved as vaccine candidates by creating additional mutations within each strain that will serve to enhance the safety and immunogenicity of the vaccine.

With regard to safety, a second mutation can be introduced into the recA gene of any of the strains described above, which mutation is designed to inactivate that recA gene. Such double mutant strains will therefore be defective in recombination and will be unable to recombine with wild type strains of V. cholerae in the environment. Thus, they will be incapable of acquiring wild type toxin genes and expressing the CTX element.

Immunogenicity can also be improved by introducing additional mutations into each strain which will allow that strain to express cholera toxin related antigens (e.g., the B subunit of cholera toxin) or other heterologous antigens, e.g., the nontoxic B subunit of Shiga-like toxin or various CFA antigens of enterotoxigenic E. coli strains (Karjalainen et al., 1989, Infect. Immun. 57:1126; Perez-Casal et al., 1990, Infect. Immun. 58:3594).

Thus, a series of mutated derivatives can also be useful in the invention, each incorporating additional properties that render the strains safer, genetically more stable and more broadly immunogenic. The construction of such derivatives is described below.

Construction of recA/ctxB Alleles

Cholera toxin B subunit is known to be a nontoxic, highly immunogenic molecule that is capable of inducing cholera toxin neutralizing antibodies. In order to generate more immunogenic vaccine strains, a new copy of the ctxB gene was introduced into the vaccine strains containing the Type-2 deletions described above (because Type-2 deletions remove all of the coding sequence for the cholera toxin B subunit). This was accomplished in a series of steps that are described below.

First, a promoterless copy of the ctxB gene was constructed using the polymerase chain reaction (PCR). For PCR, the downstream primer was designed so that the ctxB coding sequence could be synthesized in such a way as to eliminate the attRS1 site that lies just downstream from the stop codon in the ctxB gene. This primer had the following sequence: 5'-GGGCTAAAGTTAAAAGACAAAT-ATTTTCAGGC-3' [SEQ.ID.NO:5]. The upstream primer was designed so that only the last 24 carboxyterminal amino acid residues of the A2 subunit could be encoded by the product of the reaction. This primer had the following sequence: 5'-GGGTAGAAGTGAAACGGGGTTTACCG-3, [SEQ.ID.NO:6]. All other nucleotides in the DNA encoding the A subunit were excluded from the reaction. The DNA encoding the carboxyterminal amino acids of CtxA2 were retained in the final product to allow for translational coupling of ctxB gene expression. Since the toxic activity associated with cholera toxin is derived from the CtxA1 polypeptide, all sequences encoding the A1 polypeptide were excluded from the PCR reaction.

Figure 1:
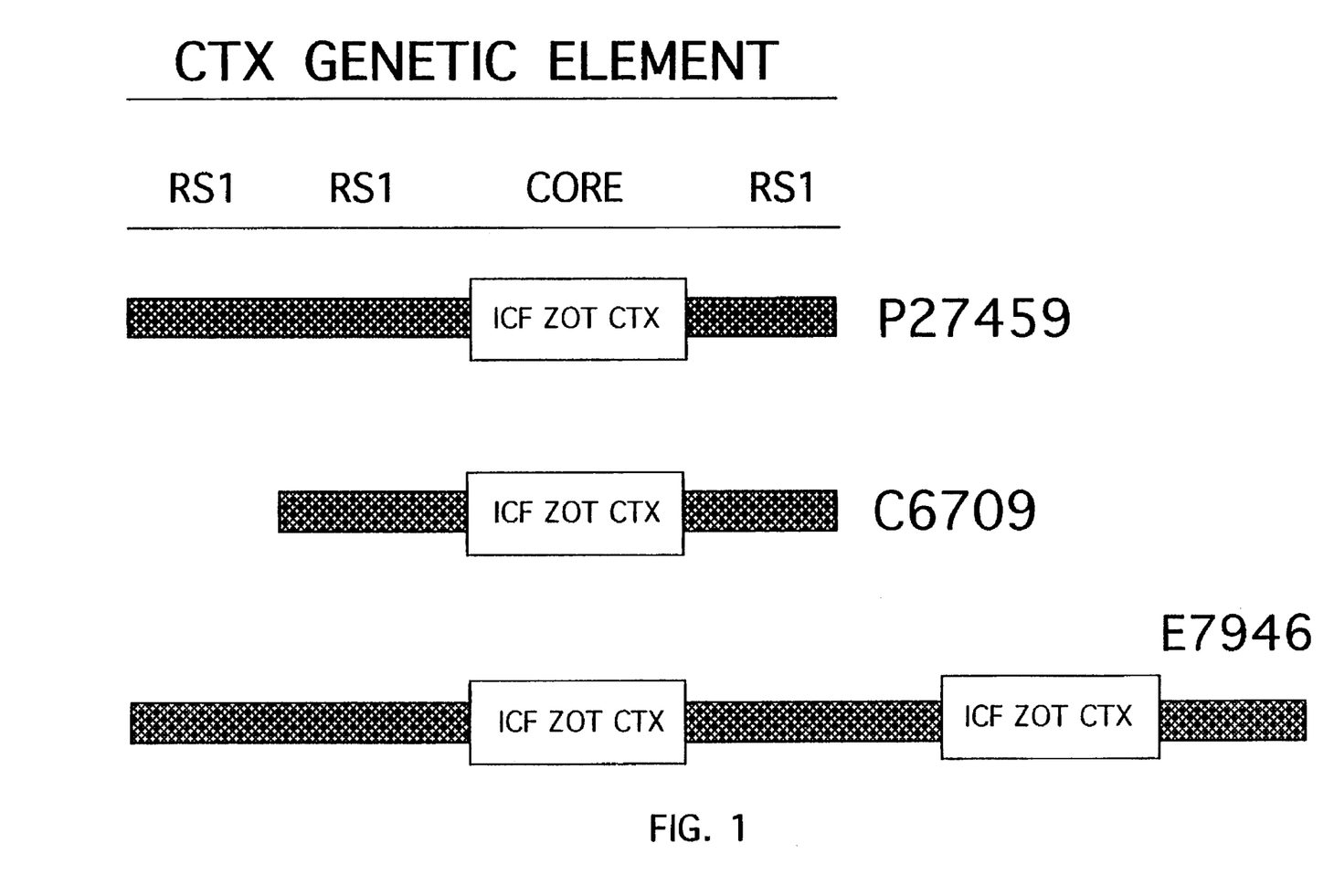
Figure 2A:
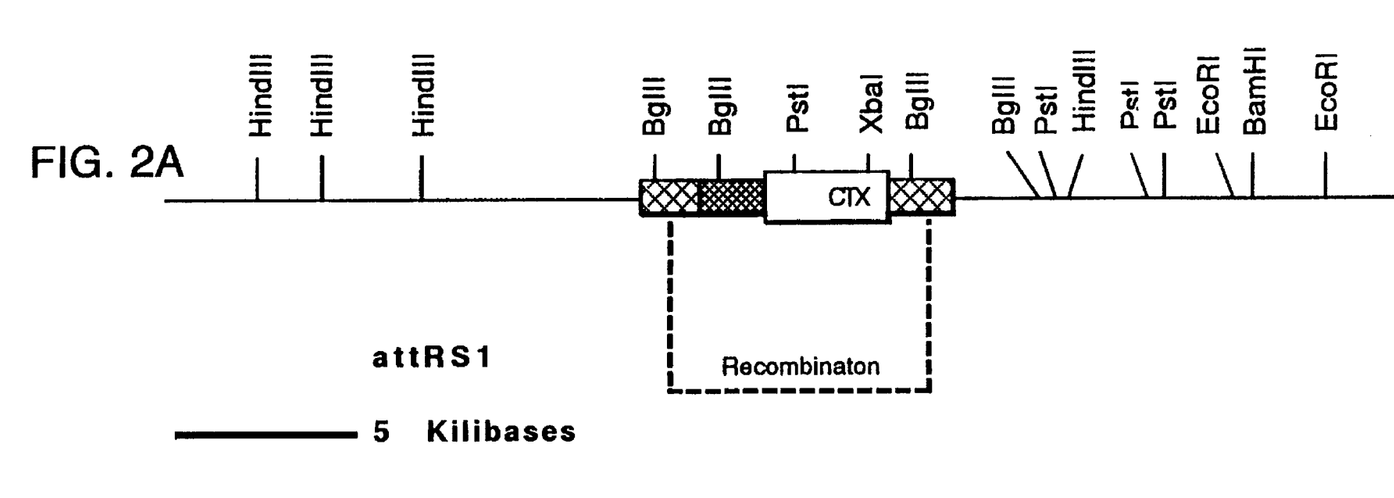
(FIG. 2A) Restriction map of the chromosome containing the CTX region from strain C6709-Sm with the CTX element schematically shown as in FIG. 1. Not shown are the restriction maps of strain P27459-Sm and E7946-Sm which are the same except for the variation observed in sites that map within the CTX element's core or RS1 sequences as designated schematically in FIG. 1.
Figure 2B:
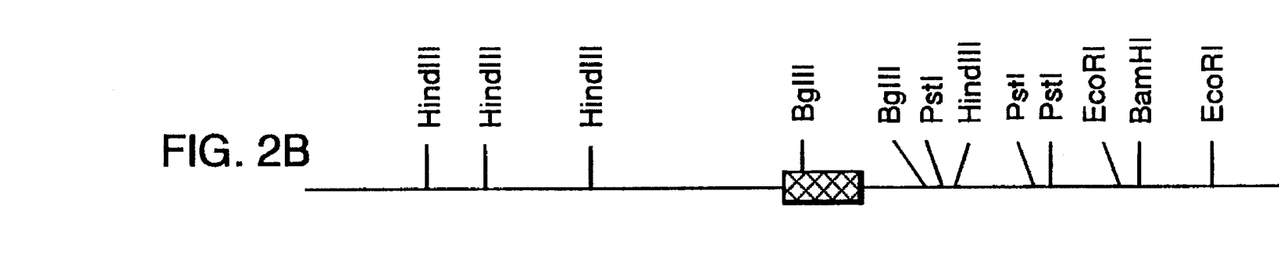
(FIG. 2B) Restriction map of corresponding chromosomal region of strain Bang-1, Bah-1, and Peru-1.
Figure 3A:
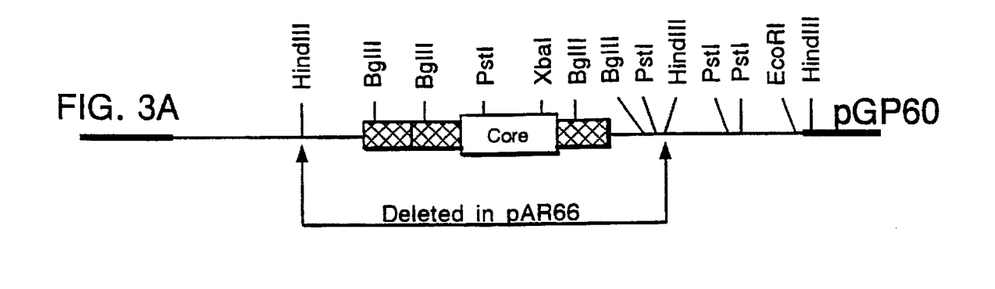
(FIG. 3A) Restriction map of plasmid pGP60 that carries an inserted DNA fragment corresponding to the chromosome containing the CTX region from strain P27459-Sm with the CTX element schematically shown as in FIG. 1. Below this is a two headed arrow which designates the DNA which has been deleted in plasmid pAR62.
Figure 3B:
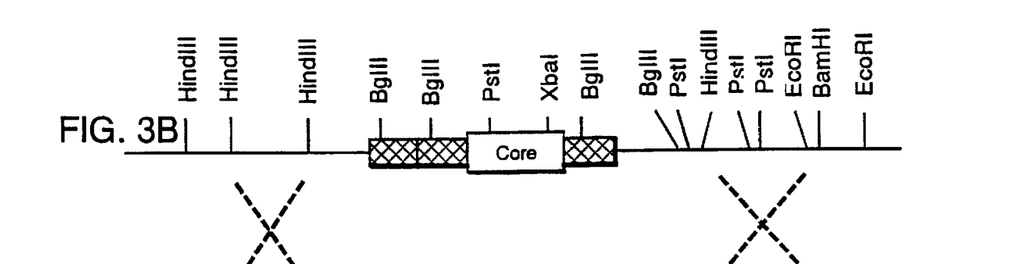
(FIG. 3B) The restriction map of the CTX region of strain P27459-Sm is shown including restriction sites that map outside the region cloned on plasmid pGP60.
Figure 3C:
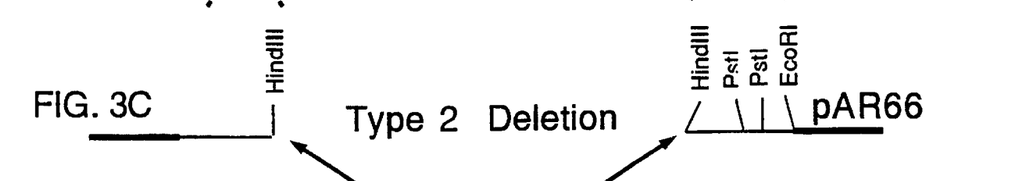
(FIG. 3C) A demonstration of the recombinational events (broken lines) between plasmid pAR62 and the chromosome that produced the Type-2 deletion which gave rise in parental strains C6709-Sm, P27459-Sm and E7946-Sm to deletion mutants Peru-2, Bang-2, and Bah-2, respectively.
Figure 3D:
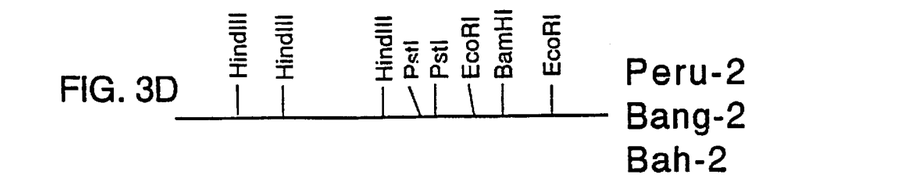
(FIG. 3D) Restriction map of the chromosome of strains Peru-2, Bang-2, and Bah-2.
Figure 4:
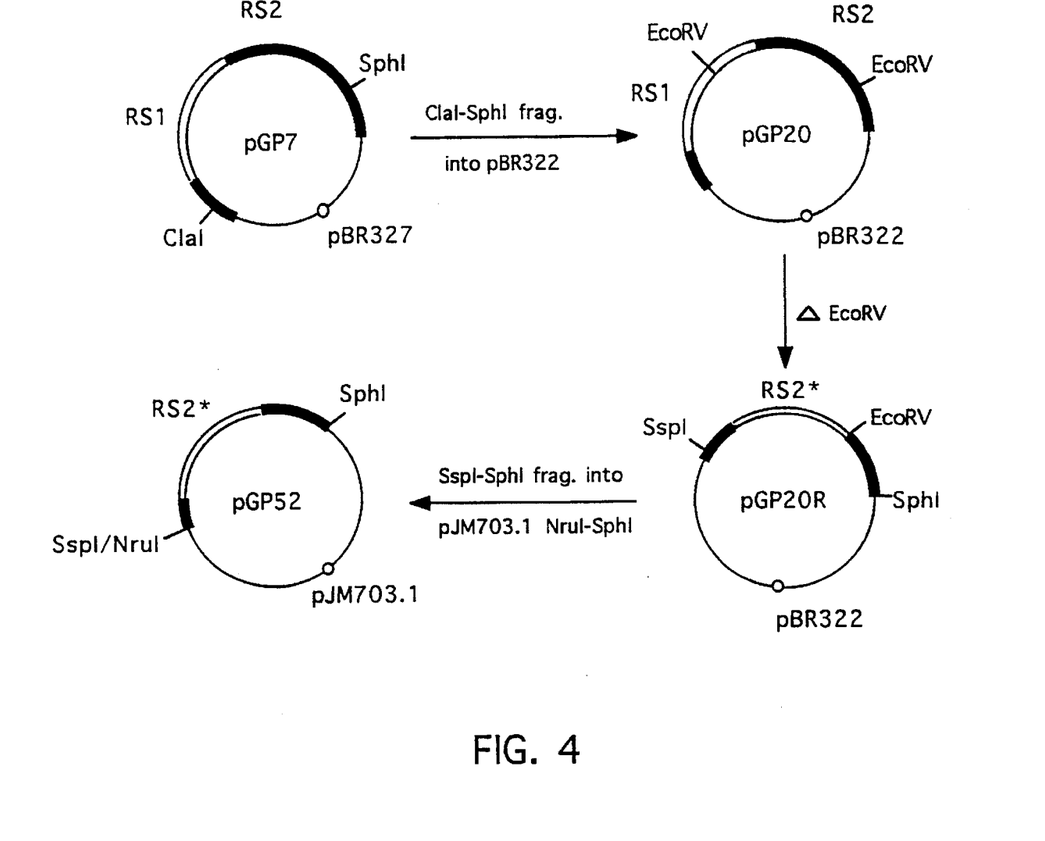
FIG. 4 is a diagrammatical representation of the construction of plasmid pGP52.
Figure 5:
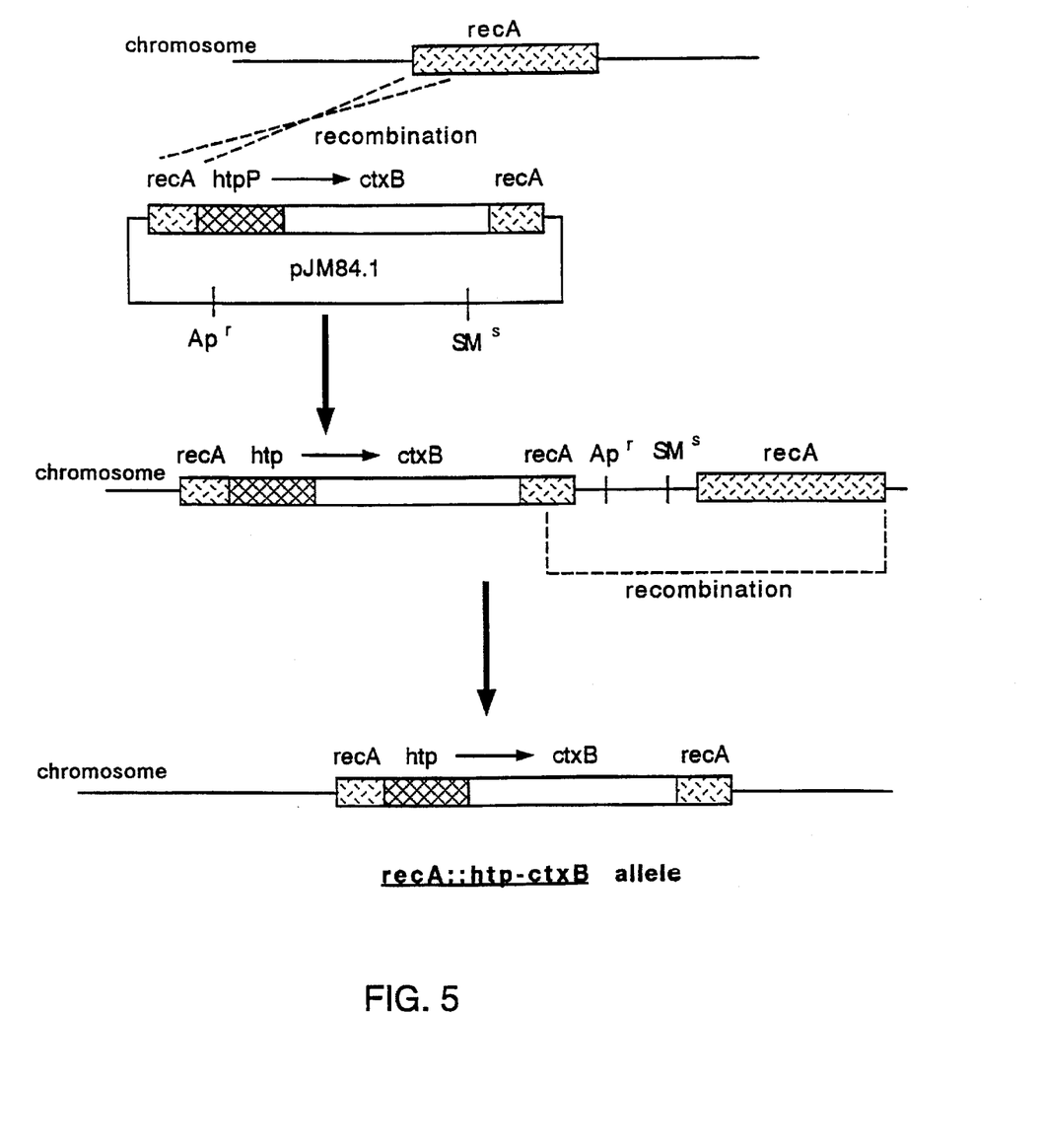

PCR was performed using the ctxB primers as described above using V. cholerae DNA from the Peruvian strain, C6709-Sm (FIG. 5). The product of the reaction, a 0.6 kilobase pair fragment, was cloned into plasmid pCR100. This fragment was then cut out of the plasmid as a 0.6 kilobase pair SpeI-EcoRI fragment and was cloned into two individual acceptor plasmids, XbaI-EcoRI digested pRT41 and XbaI-EcoRI digested pVC100. The resulting plasmids, pJM411 and pJM1001, then each encode a copy of the ctxB gene under the control of either the ctx promoter (ctxP) or the htpG promoter (hptP) of V. cholerae, respectively. These plasmids were then transferred to the nontoxigenic strain V. cholerae 0395-NT (Mekalanos et al., 1983, Nature 306:551 and U.S. Pat. No. 4,935,364), generating two new strains termed 0395-NT pJM411 and 0395-NT pJM1001. The amount of cholera B subunit produced by each strain was measured by GM1 ELISA. Strain 0395-NT pJM411 produced 30 μg/ml, while strain 0395-NT pJM1001 produced 100 μg/ml in LB culture supernatant fluids. These results demonstrate that the PCR product was a functional ctxB gene encoding an antigenic cholera B subunit capable of binding to ganglioside GM1 and was therefore similar to that secreted by normal wild type V. cholerae.

Figure 6:
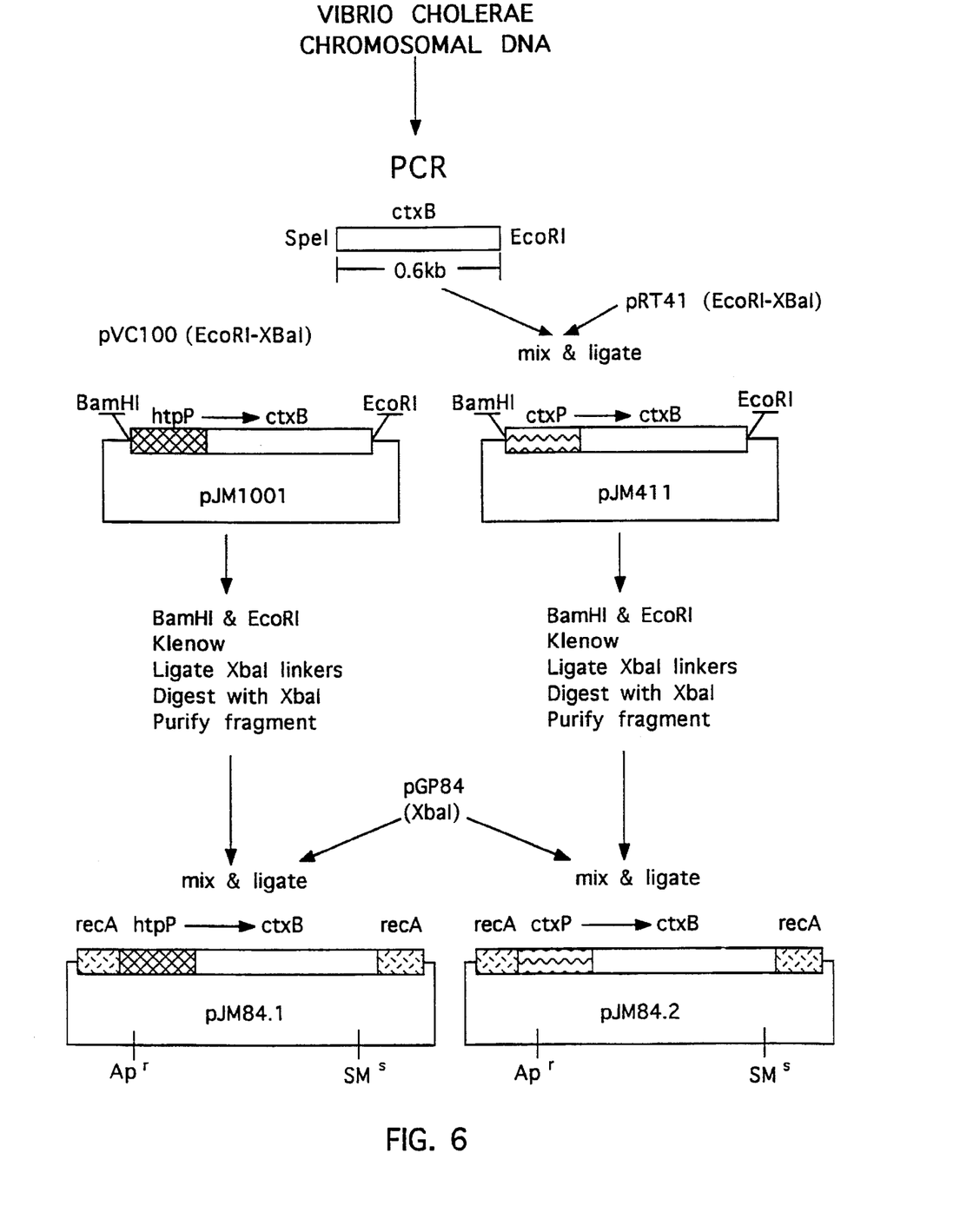

In the next step, EcoRI-BamHI fragments of DNA specifying the promoter-ctxB constructs were subcloned into the suicide recA plasmid pGP84. This plasmid contains a V. cholerae chromosomal DNA insert that corresponds to the DNA which flanks the recA gene of V. cholerae (i.e., an internal deletion of recA). Plasmid pGP84 is a derivative of suicide plasmid pJM703.1 (Miller et al., 1988, J. Bacteriol. 170:2575) and encodes sequences corresponding to the flanking regions of the recA gene of V. cholerae (Goldberg et al., 1986, J. Bacteriol. 165:715) including a BglII-PvuII fragment on the left side and an XbaI-EcoRI fragment on the right side. A 1.3 kb fragment encoding kanamycin resistance is positioned between these two fragments. Plasmid pGP84 also contains a NruI-BamHI fragment encoding sensitivity to streptomycin. This latter fragment is derived from plasmid pNO1523 (Dean, 1981, Gene 15:99). When pGp84 is digested with XbaI, the 1.3 kb fragment is removed and other XbaI fragments can be inserted into this deleted recA region. The subcloning was accomplished as follows: Each 
of the two EcoRI-BamHI fragments specifying the promoter-ctxB constructs were modified by the addition of XbaI linkers. They were individually ligated to XbaI digested pGP84 to generate two new plasmids pJM84.1 and pJM84.2, each of which contains DNA specifying the htpP-ctxB and the ctxP-ctxB constructs respectively (FIG. 6).

Next, plasmids pJM84.1 and pJM84.2 were transferred into *V. cholerae* strains Peru-2, Bang-2 and Bah-2 and ampicillin resistant colonies were selected. Because these plasmids are incapable of replication in *V. cholerae*, they integrate into the host cell chromosome by homologous recombination generating the structure shown in FIG. 6. Both plasmids also encode a gene for streptomycin sensitivity which allows for positive selection against a plasmid integration event in strains that are streptomycin resistant (i.e., strains Peru-2, Bang-2 and Bah-2). Thus, when strains that have a plasmid integrated into the chromosomal DNA are grown on medium containing 2 mg/ml streptomycin, colonies that have reverted to ampicillin sensitivity can be isolated. Strains that had now crossed out the integrated plasmid in such a way as to leave behind the recA deletion mutation together with the ctxB construct were then selected from among these latter strains. These strains were easily identified as having the following properties:

1. They were ampicillin sensitive.
2. They were killed in the presence of 0.1 ml methyl methane sulfonate per ml of LB, a characteristic phenotype of $recA^-$ cells.
3. They produced the cholera B subunit as measured by GMI-ELISA.
4. Southern blot analysis using recA and ctxB probes confirmed that they contained DNA fragments consistent with the presence of the ctxB construct and deletion of the appropriate recA sequences.

Bacterial strains that were isolated following the procedure described above are as follows:

| STRAIN | GENOTYPE |
|---|---|
| Peru-3 | attRS1 deletion, recA::htpP-ctxB,str |
| Peru-4 | attRS1 deletion, recA::ctxP-ctxB,str |
| Peru-3 | attRS1 deletion, recA::htpP-ctxB,str |
| Bah-3 | attRS1 deletion, recA::htpP-ctxB,str |
| Bah-4 | attRS1 deletion, recA::ctxP-ctxB,str |

Construction of lacZ-ctxB Alleles

The recA mutation contained within the vaccine strains described above renders the strains deficient in homologous recombination. In order to produce candidate vaccines that were still capable of homologous recombination, the ctxB gene was inserted into the lacZ gene of *V. cholerae* as described below.

The plasmid pCG698 which encodes the lacZ gene of *V. cholerae,* contains a unique HpaI site in the middle of the lacZ coding sequence. The plasmid pCG698 was constructed as follows: The β-galactosidase gene of *V. cholerae* was cloned from a library of chromosomal DNA fragments from strain E7946 as described (Mekalanos, 1983, Cell 35:253). It was found to express β-galactosidase and following restriction enzyme mapping, was found to contain a 6 kb insert containing 2 HpaI sites in the lacZ gene each of which was separated by 2.1 kb of DNA. This plasmid was linearized with HpaI and XbaI linkers were ligated to the ends. An EcoRI-BamHI fragment containing the ctxP-ctxB construct was removed from pJM411 as described above, the ends were modified by the addition of XbaI linkers and the fragment was ligated into the similarly modified pCG698. The resulting plasmid pJM6891, now contained the ctxP-ctxB construct inserted into the middle of the lacZ gene. This plasmid was transferred into *V. cholerae* strains Peru-2, Bang-2 and Bah-2 and each resulting strain was screened for growth in the presence of X-gal. White colonies containing an inactivated lacZ gene were picked and purified. Strains that contained an integrated copy of the lacZ::ctxP-ctxB sequences into the host cell chromosome were obtained by curing the bacteria of pJM6891 by growth in the absence of ampicillin. The presence of the appropriate sequences was confirmed by Southern blot analysis and the ability of these bacteria to produce cholera toxin B subunit was confirmed by GMI-ELISA. Bacterial strains isolated following this procedure are as follows:

| STRAIN | GENOTYPE |
|---|---|
| Peru-5 | attRS1 deletion, lacZ::ctxP-ctxB,str |
| Bang-5 | attRS 1deletion, lacz::ctxP-ctxB,str |
| Bah-5 | attRS1 deletion, lacz::ctxP-ctxB,str |

In order to characterize some of these carrier cholera vaccine candidates with regard to mouse colonization, mice were infected with the strains listed below. The strain TCP2, a derivative of 0395-N1 which contains a TcpA deletion and does not colonize the intestine of human volunteers, served as a control. Five mice were used for each strain. At 24 hours post-infection, the upper intestine was removed from each mouse, homogenized and assayed for the number of *V. cholerae* present using a simple plating assay. The results are presented in the table below. Essentially, no TCP2 bacteria were detected in the intestines of mice infected with TCP2 and thus the values given below represent the number of bacteria of each strain that colonized the mouse intestine above a background level of zero.

| Strain | CFU per mouse[a] | Genotype/Construct[b] | | |
|---|---|---|---|---|
| Peru-3 | $9.4 \times 10^5$ | attRS1 deletion | #2, | recA::htpG-ctxB |
| Peru-2 | $2.5 \times 10^6$ | attRS1 deletion | #2, | |
| Peru-4 | $6.0 \times 10^6$ | attRS1 deletion | #2 | recA::ctx-ctxB |
| Peru-5 | $6.6 \times 10^6$ | attRS1 deletion | #2 | lacZ::ctx-ctxB |
| Bang-2 | $9.9 \times 10^6$ | attRS1 detetion | #2, | |
| Bang-3 | $2.7 \times 10^7$ | attRS1 deletion | #2, | recA::htpG-ctxB |

[a]Cotony forming units recovered per mouse (average of five mice).
[b]The construct att RS1 deletion #2 is a Type 2 deletion constructed with plasmid pAR62, described in FIG. 3.
The construct recA::htpG-ctxB is a deletion of the recA gene and insertion of the cholera toxin B subunit gene under control of the heat shock promoter derived from the htpG of *V. cholerae*.
The construct recA::htpG-ctxB is a deletion of the recA gene and insertion of the cholera toxin B subunit gene under control of the cholera toxin promoter derived from the ctx gene of a hypertoxigenic strain 569B of *V. cholerae*.
The construct lacZ::ctx-ctxB is an insertion in the lacZ gene of *V. cholerae* that is composed of the cholera toxin B subunit gene under control of the cholera toxin promoter derived from the ctx gene of a hypertoxigenic strain 569B of *V. cholerae*.

The results suggest that the presence of the recA::htpP-ctxB allele serves to reduce the ability of the Peru-derived strains to colonize the intestine (compare, for example, Peru-3 with Peru-2). However, the effect of this construct on colonalization of the Bang-derived strain was less marked (compare Bang-3 with Bang-2). In general, introduction of the constructs wherein ctxB is under the control of its own promoter had less effect on colonalization that the constructs wherein it was placed under the control of the heat shock promoter. It should be noted that strains Peru-2, Peru-3 and Bang-3 vary in their colonalization properties over a 28-fold range. It is well within the art following the protocols described above, to isolate additional vaccine candidates that vary even more widely in their colonalization properties.

The procedures described above can be applied by any artisan skilled in the art for the construction of derivatives of Peru-2, Bang-2 and Bah-2 which are capable of expressing a wide variety of foreign or heterologous antigens, e.g., antigens that are not normally expressed in *V. cholerae*. Such derivatives, when used as live vaccines would be expected to induce a strong immune response against both *V. cholerae* antigens and the foreign antigen that it encodes. Both systemic and local immune responses will likely be induced because vaccination with other prototype *V. cholerae* vaccines has resulted in the induction of circulating IgG and local IgA antibodies that are specific for both whole cell antigens (e.g., LPS) and as well as individual proteins such as cholera toxin B subunit (Herrington et al., 1988, J. Exp. Med. 168:1487–1492). A foreign antigen expressed by *V. cholerae* would be expected to elicit an immune response similar to that of the individual cholera proteins.

The methods useful for the introduction of heterologous antigens into *V. cholerae* are similar to those described above for the re-introduction of the ctxB gene into vaccine strains Peru-3, Peru-4, Peru-5, Bang-3, Bah-3 and Bah-4. Virtually any heterologous antigen can be inserted into *V. cholerae* using these methods.

In summary, the data demonstrate the feasibility of using genetic engineering techniques to generate novel ctxB-containing *V. cholerae* strains wherein the expression of the ctxB gene is placed under the control of either of two *V. cholerae* promoters (ctxP and htpP). The engineered genes can be recombined into the *V. cholerae* chromosome into target genes such as recA or lacZ to generate strains which stably express large amounts of cholera toxin B subunit (for example, strains Peru-3, Peru-4 and Peru-5). The same protocol can be used to construct derivatives of Peru-2, Bang-2 and Bah-2 which are capable of expression virtually any heterologous antigen or antigens normally encoded by either bacteria, viruses, or parasites. The methods described in the invention therefore teach generation of a multivalent *V. cholerae* vaccine "carrier strain" which can be manipulated to encode and express other antigens and can be administered to humans in order to immunize them against not only cholera, but other pathogens as well.

Use of the Live Vaccine Strains

The *V. cholerae* mutant strains Peru-1, Peru-2, Bang-1, Bang-2, Bah-1 and Bah-2 and the additional mutants described above are useful as sources of immunological protection against cholera and other related toxigenic diseases when used as live vaccines. Other such diseases include, but are not limited to, those induced by enterotoxigenic *E. coli* and other bacteria that produce toxins which are immunologically cross-neutralizable with cholera B subunit.

When inoculated into the intestine of an experimental animal or human, mutant strains of *V. cholerae* should stimulate and induce a strong immunological response against all bacterial components that are elaborated by these strains including, but not limited to, the Ogawa and Inaba 01 LPS antigens, flagella antigens, the antigenic domains of the Tcp pili, and the outermembrane proteins. Based on published studies with other prototype cholera vaccines, both IgA and IgG classes of antibodies directed against these bacterial components will be synthesized in the inoculated animal or human and will serve to protect the animal or human against subsequent challenge with virulent strains of *V. cholerae*.

Dosage

Determination of the appropriate dosage and administration of these vaccines is performed essentially as described in Herrington et al., (1988, J. Exper. Med. 168:1487–1492). In general, such dosages are between, but are not limited to, $10^5$–$10^9$ viable bacteria per dose.

Growth of Vaccine Strains

The bacteria to be used as the vaccine can be grown in a standard *V. cholerae* laboratory media. The cells can be harvested and then lyophilized in a formulation that preserves viability (e.g., sterile skim milk or saline containing 5 mM $CaCl_2$ and 10% weight by volume of glycerol).

Administration

Administration of the vaccine involves combining the contents of two envelopes or vials, one containing the lyophilized vaccine strain, the other containing water and sufficient sodium bicarbonate or alternate buffer as to neutralize stomach acid (approximately 2 grams). The vaccine can then be swallowed by the vaccinee. Alternatively, the lyophilized vaccine can be incorporated into tablets which can be coated with an acid resistant "enteric coating". Such a form of vaccine can be administered to the vaccinee in one or more (up to three) doses spaced from a few days to several weeks apart. When used as a "booster" vaccine, the vaccine can also be administered to previously vaccinated individuals in one or more doses (up to three) spaced from a few days to several weeks apart.

Improved Killed Oral Cholera Vaccines

Preparations of improved killed oral cholera vaccines can be made from the strains described above. The experimental cholera vaccine that is currently available is comprised of approximately $10^{11}$ formalin and heat killed *V. cholerae* cells mixed with purified cholera toxin B subunit (Black et al., Infect. Immun. 55:1116, 1987). The four strains that are used in the preparation of the bacterial component of this vaccine produce active cholera toxin which must be completely inactivated before administration to the vaccinee. The new strains described above provide a vaccine that is vastly improved compared with the vaccine of Black et al. (Supra) for each of the reasons given below.

(1) Because the strains derived from, and including Peru-2, Bang-2 and Bah-2, produce only the nontoxic B subunit of the cholera toxin and not the toxic A subunit, cultures of these strains require only mild inactivation prior to administration to a vaccinee, thus avoiding the more severe denaturing treatments such as formalin or heat. The advantages of the milder treatment are that the antigens will retain a greater degree of their native configuration and as a result they will be more immunogenic. Mild methods of inactivation that avoid chemically inactivating the bacterial proteins include microwaving the organisms, treatment with another radiation source or a mild organic solvent or detergent, or the cells may be lysed by mechanical methods such as sonication or use of a French Press.

(2) In the strains Peru-3, Bang-3 and Bah-3, the ctxB gene has been placed under the control of the htp promoter. As a result, these strains synthesize large quantities of the cholera toxin B subunit (greater than 10 µg/ml of culture) in standard laboratory medium such as LB. This facilitates purification of large amounts of the cholera B subunit and thus these strains provide a significant advantage over other strains which only produce the B subunit in small quantities under stringent growth conditions.

(3) In the preparation of existing killed cholera vaccines, a separate bacterial strain is used to produce the B toxin subunit from the strain used as the whole cell antigen. During preparation of the B subunit it is therefore necessary to purify the B subunit away from the toxic A subunit using biochemical methods. Such purification incurs the risk that small amounts of the A subunit may contaminate the prepa- 
ration of the B subunit. Using the strains described above, it is possible to generate a whole cell antigen preparation from the same culture used to obtain the B subunit preparation. In the first instance, purification of the B subunit is now unnecessary because the strain does not produce the A subunit, thus reducing the amount of time and considerable expense involved in production of the vaccine. Secondly, there is no risk of having any contaminating A subunit in the preparations since the bacteria simply do not encode the gene for this subunit and therefore cannot produce it. The whole cell preparation can therefore be used as a vaccine with minimal risk to the vaccinee.

(4) The bacterial strains that are the subject of the instant invention are all derivatives of *V. cholerae* of the El Tor biotype and more particularly, in the case of Peru-2, Peru-3 and Peru-4, they are derivatives of an isolate (C6709-Sm) which is in fact the causative agent of the current epidemic in Latin America. If there are antigens that are unique to this particular parental strain, the vaccine derivatives described above may provide generally better protection against El Tor disease in Latin America and possibly other areas in the world.

Preparation of Improved Oral Killed Cholera Vaccines

An improved oral killed cholera vaccine can be prepared as follows. A minimum of two strains, one belonging to the Ogawa serotype (e.g., Bah-3) and the other belonging to the Inaba serotype (e.g., Peru-3 or Bang-3) can be grown in separate cultures. One of ordinary skill in the art will know how to adjust the conditions, media, etc. to maximize cell growth at 37° C. For example, cultures grown under a high level of aeration in a medium such as CYE (Mekalanos et al., 1977, Infect. Immun. 16:789) or minimal medium containing glucose, i.e., AGM4 (van de Walle et al., 1990, Appl. Microbiol. Biotechnol. 33:389) can be used. When growth of the bacteria has reached saturation, whole cells can be recovered from the medium by centrifugation, while proteins (including the B subunit) contained within the supernatant fraction can be obtained by ultracentrifugation or by precipitation. The cells can be inactivated using the methods of Black et al. (Infect. Immun. 55:1116, 1987) or by milder methods (e.g., microwaving, irradiation using alpha, beta or gamma rays), treatment with organic solvents such as ethanol or acetone, or they may be lysed by treatment with either a detergent or by mechanical methods, such as sonication or by using a French Press. The inactivated cells can then be combined with filtered, concentrated supernatant containing bacterial proteins (including subunit B) and the mixture can be suspended in a pharmaceutically acceptable solution appropriate for oral administration (e.g., sterile saline or 2% sodium bicarbonate).

Administration

The vaccine can be administered to the vaccinee as an oral saline solution which is swallowed by the vaccinee several minutes after the vaccinee has ingested 2 grams of sodium bicarbonate. Alternatively, the preparation can be lyophilized and compressed into tablets which are then coated with an acid-resistant "enteric coating" prior to administration to the vaccinee. The tablets can also be microencapsulated with polymers in order to facilitate uptake of the preparation by the intestinal mucosal tissue.

Dosage

A single dose of vaccine should contain approximately $10^{11}$ cells and approximately 100–5000 μg of cholera B subunit. It is expected that the vaccinee will require approximately two or more separate doses of vaccine administered approximately two or more weeks apart.

Deposit

Under the terms of the Budapest Treaty on the International Recognition of the Deposit of Microorganisms for the Purpose of Patent Procedure, deposit of *V. cholerae* strains C6709-Sm, P27459-Sm and E7946-Sm has been made with the American Type Culture Collection (ATCC) of Rockville, Maryland, USA, where the deposits were given ATCC Accession Numbers ATCC 55331 (C6709-Sm); ATCC 55333 (P27459-Sm); and, ATCC 55332 (E7946-Sm).

The following *V. cholerae* strains were also deposited and given ATCC numbers: Bah-2 (ATCC 55859); Bah-3 (ATCC 55860); Bang-2 (ATCC 55862); Bang-3 (ATCC 55863); Peru-2 (ATCC 55865); Peru-3 (ATCC 55866); Peru-4 (ATCC 55867); and Peru-5 (ATCC 55868).

Applicant's assignee, President and Fellows of Harvard College, represents that the ATCC is a depository affording permanence of the deposit and ready accessibility thereto by the public if a patent is granted. All restrictions on the availability to the public of the material so deposited will be irrevocably removed upon granting of a patent. The material will be available during the pendency of the patent application to one determined by the Commissioner to be entitled thereto under 37 C.F.R. 1.14 and 35 U.S.C. § 122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

I claim:

1. A nontoxinogenic genetically stable mutant strain of *Vibrio cholerae*, said strain comprising a genetically engineered deletion of DNA encoding ctxA subunit such that said strain lacks a reactogenic subunit A of cholera toxin, said strain further comprising deletions of attRS1 sequences, and having at least 1000-fold lower attRS1 mediated site-specific recombination relative to a parent strain having at least two copies of attRS1.

2. The *Vibrio cholerae* strain of claim 1, wherein said strain is derived from a parental strain belonging to the El Tor biotype.

3. The *Vibrio cholerae* strain of claim 2, wherein said strain is derived from a parental strain belonging to the Inaba or Ogawa serotype.

4. The *Vibrio cholerae* strain of claim 3, wherein said strain is Peru-2, Bang-2 or Bah-2.

5. The *Vibrio cholerae* strain of claim 1, wherein said strain comprises a deletion of CTX core sequences and and is fully deleted for all said attRS1 sequences.

6. The *vibrio cholerae* strain of claim 1, wherein said strain further lacks a recA gone such that 0.1 µl methyl methane sulfonate per one of Luria Broth is lethal to said strain.

7. The *Vibrio cholerae* strain of claim 1, 5 or 6, wherein said strain further encodes a B subunit of cholera toxin.

8. The *Vibrio cholerae* strain of claim 1, 5 or 6, wherein said strain further encodes a heterolugous antigen.

9. The *Vibrio cholerae* strain of claim 8, wherein the DNA sequence encoding said heterologous antigen is inserted into the lacZ gene of *Vibrio cholerae*.

10. The *Vibrio cholerae* strain of claim 7, wherein said strain is Peru-3, Peru-4, Bang-3, Bah-3 or Bah-4.

11. A method making a genetically stable mutant strain of *Vibrio cholerae* comprising a deletion of DNA encoding the ctxA subunit such that said strain lacks a reactogenic subunit A of cholera toxin, and said strain further comprising deletions of attRS1 sequences, said method comprising introducing into a wild type *Vibrio cholerae* a plasmid comprising a fragment of *Vibrio cholerae* DNA which is mutated in its ctxA and attRS1 sequences, said DNA being capable of recombining with wild type *Vibrio cholerae* DNA inside said wild type *Vibrio cholerae* resulting in the generation of said mutant strain, said mutant strain having at least 1000-fold lower attRS1 mediated site-specific recombination relative to a parent strain having at least two copies of attRS1.

12. The method of claim 11, wherein said *Vibrio cholerae* strain is Peru-2, Bang-2 or Bah-2.

13. The method of claim 11, wherein said mutant strain lacks CTX core sequences and all attRS1 sequences.

14. The method of claim 11, wherein said mutant strain further lacks a recA gone such that 0.1 µl methyl methane sulfonate per one of Luria Broth is lethal to said strain.

15. The method of claim 2, wherein said mutant strain further encodes a heterologous antigen.

16. The method of claim 2, wherein said method further comprises introducing into the lacZ gene of said mutant strain a fragment of DNA encoding an antigen.

17. The method of claim 16, wherein said mutant strain is Peru-5.

18. A killed oral cholera vaccine, said vaccine comprising at least a first and a second *Vibrio cholerae* strain at least one strain of which is a strain of claim 1, suspended in a physiologically acceptable carrier, wherein each strain comprises a genetically engineered deletion of DNA encoding a ctxA subunit such that said strain lacks a reactogenic subunit A of cholera toxin, and wherein at least two of said strains are different serotypes, said *Vibrio cholerae* being nonviable, said vaccine further comprising cholera toxin B subunit which is overproduced by at least one of said serotypes of said *Vibrio choleras* strain.

19. The vaccine of claim 18, wherein one of said serotypes is an Ogawa serotype and another of said serotypes is an Inaba serotype.

20. The vaccine of claim 19, wherein said vaccine comprises Bah-3 and either Peru-3 or Bang-3 or both Peru-3 and Bang-3.

21. A method of making a killed *Vibrio cholerae* vaccine, said method comprising the steps of providing at least the first and second *Vibrio cholerae* strains of claim 18, which strains have been killed;

adding to said killed strains cholera toxin B subunit produced by at least one of said strains, wherein said toxin B subunit is obtained from the medium in which said strain was propagated; and suspending said killed strains and said toxin B subunit in a physiologically acceptable carrier.

22. A vaccine comprising the strain of claim 1 in a physiologically acceptable carrier.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 17
( B ) TYPE: nucleic acid
( C ) STRANDEDNESS: single
( D ) TOPOLOGY: linear ( x i ) SEQUENCE DESCRIPTION: SEQ ID NO: 1:

```
CCTAGTGCGC ATTATGT                                                                            17
```

( 2 ) INFORMATION FOR SEQ ID NO: 2:

( i ) SEQUENCE CHARACTERISTICS:
        ( A ) LENGTH: 52
        ( B ) TYPE: nucleic acid
        ( C ) STRANDEDNESS: single
        ( D ) TOPOLOGY: linear     ( x i ) SEQUENCE DESCRIPTION: SEQ ID NO: 2:

```
TAAACCTAGA GACAAAATGT TCCTAGTGCG CATTATGTAT GTTATGTTAA AT           52
```

( 2 ) INFORMATION FOR SEQ ID NO: 3:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear     ( x i ) SEQUENCE DESCRIPTION: SEQ ID NO: 3:

```
TAAACCTAGA GACAAAATGT TCCTAGTGCG CATTATGTGG CGCGGCAT               48
```

( 2 ) INFORMATION FOR SEQ ID NO: 4:

( i ) SEQUENCE CHARACTERISTICS:
        ( A ) LENGTH: 50
        ( B ) TYPE: nucleic acid
        ( C ) STRANDEDNESS: single
        ( D ) TOPOLOGY: linear     ( x i ) SEQUENCE DESCRIPTION: SEQ ID NO: 4:

```
AAACCCTAGA TTCCGCCGCC TTAGTGCGCA TTATGTATGT TATGTTAAAT             50
```

( 2 ) INFORMATION FOR SEQ ID NO: 5:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear     ( x i ) SEQUENCE DESCRIPTION: SEQ ID NO: 5:

```
GGGCTAAAGT TAAAAGACAA ATATTTCAG GC                                 32
```

( 2 ) INFORMATION FOR SEQ ID NO: 6:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( x i ) SEQUENCE DESCRIPTION: SEQ ID NO: 6:

```
GGGTAGAAGT GAAACGGGGT TTACCG                                       26
```